United States Patent [19]

Wurster

[11] 4,141,362
[45] Feb. 27, 1979

[54] LASER ENDOSCOPE

[75] Inventor: Helmut Wurster, Oberderdingen, Fed. Rep. of Germany

[73] Assignee: Richard Wolf GmbH, Fed. Rep. of Germany

[21] Appl. No.: 799,385

[22] Filed: May 23, 1977

[51] Int. Cl.² ............................................. A61B 17/36
[52] U.S. Cl. ................................ 128/303.1; 128/395
[58] Field of Search ............... 128/303.1, 395, 396, 128/397, 398

[56] References Cited

U.S. PATENT DOCUMENTS

| | | | |
|---|---|---|---|
| 3,096,767 | 7/1963 | Gresser et al. | 128/303.1 |
| 3,456,641 | 7/1969 | Yokota et al. | 128/397 X |
| 3,556,634 | 1/1971 | Townes et al. | 128/395 X |
| 3,710,798 | 1/1973 | Bredemeier | 128/303.1 |
| 3,769,963 | 11/1973 | Goldman et al. | 128/303.1 |
| 3,783,874 | 1/1974 | Koester et al. | 128/303.1 |
| 3,796,220 | 3/1974 | Bredemeier | 128/303.1 |
| 3,804,095 | 4/1974 | Bredemeier | 128/303.1 |
| 3,865,114 | 2/1975 | Sharon | 128/303.1 |
| 3,906,953 | 9/1975 | Wallace et al. | 128/303.1 |

*Primary Examiner*—Lee S. Cohen
*Attorney, Agent, or Firm*—Kinzer, Plyer, Dorn & McEachran

[57] ABSTRACT

Endoscope equipped both with an observation optic and a Laser beam, including a deflectable reflector enabling the laser beam to scan the body tissue and a focus enabling the laser beam focal plane to be varied depthwise in the body tissue.

9 Claims, 6 Drawing Figures

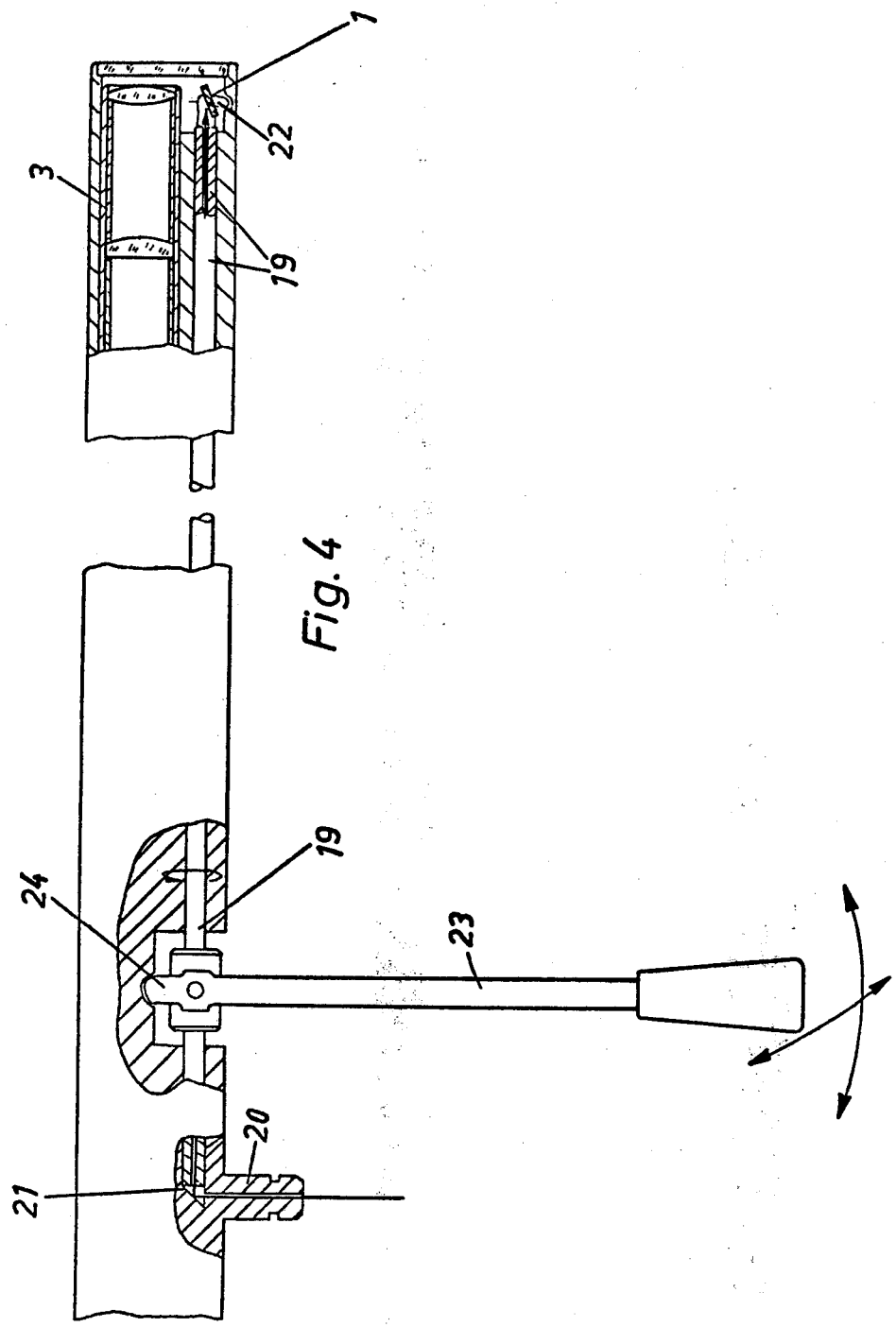

LASER ENDOSCOPE

The invention relates to an endoscope with both observation optics and a Laser device for therapy and/or coagulation of tissue parts.

The use of a Laser beam for therapy and/or coagulation of tissue parts already is known in medicine, whereby the Laser light is directed via a flexible glass fiber and a distal focusing lens to the tissue to be treated, under observation. The use of the flexible glass fiber enables the focal point of the Laser beam to be located in the viewing field of the observation optic, so that until now it was necessary to adjust the endoscope as a whole, jointly with the Laser, toward the tissue parts to be treated.

The problem addressed by the invention consists of making possible the execution of a therapeutic treatment of tissue parts by means of a Laser beam within the viewing range of the endoscope without having to effect thereby any adjusting movements of the endoscope as a whole.

According to the invention, this problem is solved by the fact that in the known endoscope mentioned initially a controllable beam deflection is provided in the beam path of the Laser, by which the Laser beam extending through the area of the endoscope shaft can scan on the object side an area within the viewing field of the observation optic or lens.

As a result, the physician has the possibility of directing the endoscope with the aid of the observation lens to the tissue field to be treated and of holding it there and of being able to direct the Laser beam to all points of the viewing field, in order to be able to perform coagulation of tissue over the entire range of the viewing field.

Thereby the Laser beam can pass adjacent to the observation lens a longitudinally oriented parallel free area of the endoscope or be reflected advantageously into the beam path of the observation lens. With this latter embodiment it is possible to reduce the diameter of the endoscope to a minimum, thereby opening up areas of applications in very small body hollows and/or cavities.

IN THE DRAWING

FIG. 4 shows a lateral view with partial axial section of an endoscope with a modified path of the Laser beam but without presentation of the ocular part.

Figure 1A:
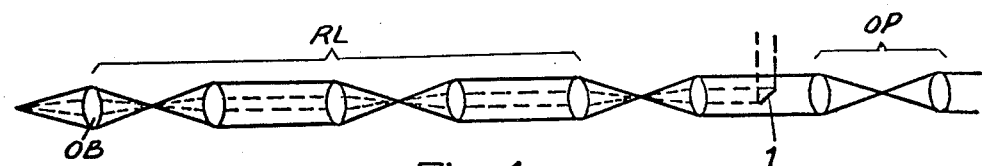
FIGS. 1a, 1b and 1c show the observation lens system of an endoscope in connection with the beam path of a Laser in the principal design and with varying the focusing of the Laser beam.
Figure 1B:
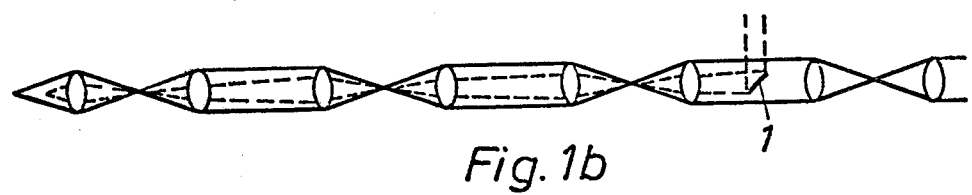
Figure 1C:
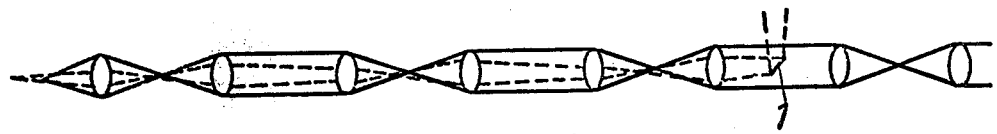
Figure 2:
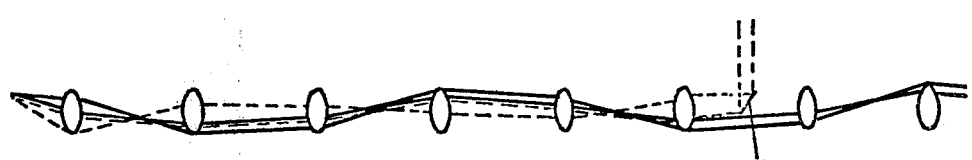
FIG. 2 shows the same representation, but with a deflected Laser beam.

The beam path of the observation optic of an endoscope is shown in FIGS. 1a to 1c in solid lines. A deflection mirror 1 is connected into this beam path of the observation optic on the proximal side for a Laser beam shown in broken lines, which is focused on the objective side (adjacent the tissue being treated) by a focusing installation in FIG. 1a into the object plane of the observation optic, and in FIGS. 1b and 1c it also is focused according to the depth of the optic, that is shifted axially. To allow for a simultaneous observation, the deflecting mirror is smaller in diameter compared to the optic and tippable to all sides, so that, according to the beam path according to FIG. 2, it is possible to deflect the Laser beam on the object side, so that as a result of this tippability of the mirror or reflector it can scan an area within the viewing field of the observation optic.

It is possible to use as the therapy Laser and/or coagulation Laser an argon Laser of high output, a YAG-Neodyme Laser or a holmium Laser. It is advantageous to focus into the beam path of the therapy Laser an He-Ne Laser as aiming installation, in order to set sights on the coagulation parts within the viewing field.

Figure 3:
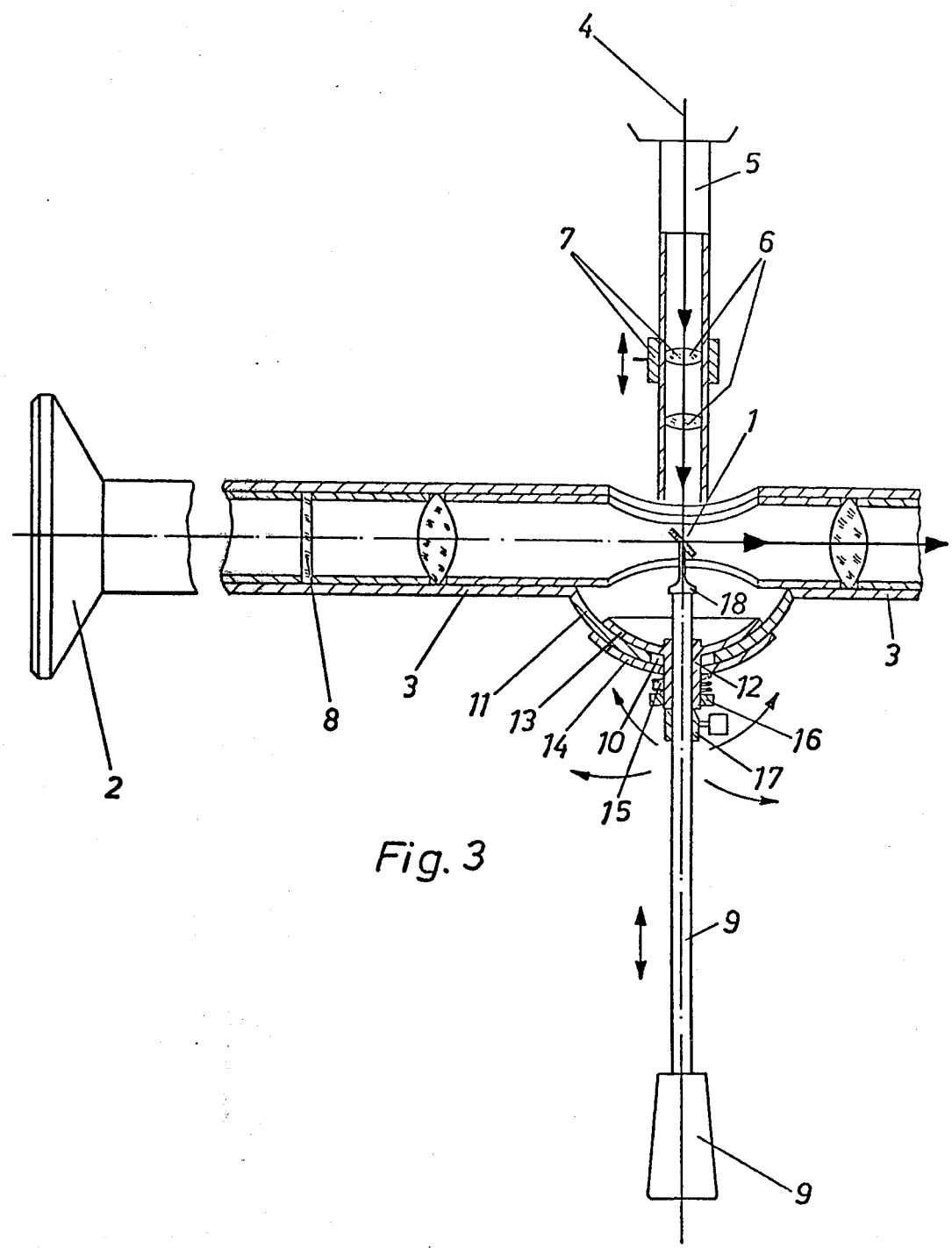
FIG. 3 shows an axial section through the proximal part of an endoscope with a Laser attachment.

In the practical embodiment, the procedure is such, for example according to FIG. 3, that the observation optic 3 provided with an ocular funnel 2 is combined with a performance Laser 4 the beam of which is transmitted through a fiber 5 and by a focusing device 6 with an axially displaceable lens 7 and via the deflection mirror 1, smaller in diameter with regard to the optic, through the objective or field lens OB of the observation optic upon the object. As a result of this smaller deflecting mirror simultaneous observation is possible. It is possible to axially shift the focusing distance of the Laser beam from the object surface of the observation optic by shifting the mirror 1, as explained from FIGS. 1b and 1c. For Laser wave lengths outside the visible range the deflection mirror is permeable only for the visible range, that is, all light outside the visible range (viz infra-red light) is reflected whilst light in the visible range is allowed to pass.

A selective filter 8 is connected between the ocular funnel 2 and the deflection mirror 1, which for the observer's protection absorbs the wave length of the Laser, but allows the remaining, visible light to pass through, so that an observation of the Laser coagulation to be performed is feasible. For direct observation the filter 8 may be pivoted out of the ray path of the observation optic and pivoted back into the beam path during the coagulation. For safety's sake the arrangement is such that the pivoting drive for filter 8 is coupled to the switch of the Laser, so that with the connection of the Laser the filter in any event is pivoted into the beam path.

So that the viewing field of the observation optic can be scanned with the Laser beam, the deflection mirror is positioned tippably to all sides and seated on the tapered end of a rod 9 to be handled. This rod 9 extends through a correspondingly wide circular opening 10 of a spherical segment 11. The center of the spherical segment 11 is located on the axis of the observation optic. The rod 9 displaceably passes through a bushing 12, to which an inner spherical segment guide 13 is connected and an outer spherical segment 14 is displaceable with the inner one. A pressure spring 15 between the spherical segment 14 and a stop 16 of the bushing 12 maintains the spherical segments 13 and 14, which cover the circular opening 10, on the inside and outside against the spherical segment 11. The rod 9 is displaced inward of the bushing 12 until the center of the deflection reflector 1 coincides with the axis of the optic. Any further inward displacement is prevented by positioning an adjustable stop 17 of the rod 9 against the proximal end of bushing 12. By pulling the rod 9 out as far as a stop 18 thereon it is possible to move the deflection reflector 1, for direct observation, out of the beam path of the optic. By either pivoting or twisting the handle 9 the deflection reflector 1 is tipped, thereby making it possible for the Laser beam to scan any part of the area within the viewing field of the observation optic.

As a result of the embodiment according to FIG. 3 it is possible to maintain the diameter of the endoscope extremely small, since the Laser beam is conducted through the relay lens system RL of the observation optic lens system OP, so that the objective (focus) of the Laser application also can be extended to the most minute human cavities.

In the embodiment according to FIG. 4, the endoscope shaft accommodates besides the observation optic 3 a longitudinally extending tube 19 in a parallel channel. The likewise focusable Laser beam, not shown, is admitted in this tube through the aperture of a stud 20 and a prism 21 in the longitudinal direction, and at the distal end it impinges on a deflection reflector 1 which allows the Laser beam to scan on the object side an area of the tissue being treated within the viewing field of the observation optic. In this case the deflection reflector 1 is fastened pivotally on a support 22 inside the shaft of the endoscope at the distal end. The reflector 1 is connected via an articulated fork to the tube 19 which is positioned longitudinally displaceably and twistably in the shaft of the endoscope. For shifting and twisting, the tube 19 is connected in an articulated manner in the area of a shaft cutout to a double arm adjustment lever 23, 24, whose shorter lever arm 24 engages pivotally into a recess. By pivoting the lever 23 the tube 19 can be shifted in a limited fashion in the longitudinal direction and rotated about its axis, with the deflection reflector 1 carrying out corresponding movements, so that it is accomplished thereby again that the Laser beam can scan on the object side an area within the viewing field of the observation optic.

I claim:

1. A combined optic endoscope and surgical Laser attachment comprising, an elongated shaft of a size for body tissue endoscopy; containing a single lens relay system including an objective lens for directing to the operation site a Laser beam while allowing simultaneous observation of the operating site through the same lens system, a Laser beam transmitting lens system positioned on said shaft and attached thereto, a manually tiltable Laser beam deflection mirror permeable to visible light located at one end of and on the axis of each of the lens relay system and transmitting lens system, said mirror being in position to receive and deflect to said lens relay system including the objective lens; the transmitted Laser beam, and an optic observation lens and related ocular on said shaft on the axis of said mirror and lens relay system and located on the side of said mirror opposite said lens relay system allowing the surgeon to observe the operation site, so that by tilting said mirror the Laser beam may be directed to any spot within the optic observation field.

2. The combination according to claim 1, characterized by the fact that the the diameter of the deflection mirror is smaller than that of the optic observation lens.

3. The combination as defined in claim 2 characterized by providing between the deflection mirror and the ocular of the optic observation lens a filter not admitting passage of the wave length of the Laser beam.

4. The combination as defined in claim 3 characterized by the fact that the deflection mirror is fastened to a manually operable rod supported on said shaft to be pivotal about its center to produce pivotal movement of the deflection mirror and also having limited mobility in its longitudinal direction to allow withdrawal of the deflection mirror from the beam path of the optic observation lens.

5. The combination as defined in claim 2 characterized by the fact that the deflection mirror is fastened to a manually operable rod supported on said shaft to be pivotal about its center to produce pivoting of the deflection mirror and also having limited mobility in its longitudinal direction to allow withdrawal of the deflection mirror from the beam path of the optic observation lens.

6. The combination as defined in claim 1, characterized by the fact that the Laser beam transmitting lens system includes a displaceable; focusing installation included as part of the combination and through which the focus plane of the Laser beam is displaceable in the direction of the optical axis of the optic observation lens.

7. The combination as defined in claim 1, characterized by the fact that the deflection mirror is fastened to a manually operable rod supported on said shaft to be pivotal about its center to pivot the mirror and also having limited mobility in its longitudinal direction to allow withdrawal of the deflection mirror from the beam path of the optic observation lens.

8. The combination as defined in claim 7, characterized by the fact that the shaft includes a fixed spherical support segment having an opening therein, said rod being supported in a bushing extending through said opening in the fixed spherical support segment, the bushing being guided by two spherical guide segments displaceably mounted on said support segment, respectively covering the opening internally and externally, the opening in said support segment being centered on the axis of the optic observation lens.

9. The combination as defined in claim 8, characterized by the rod and bushing being provided with cooperating stop means which fixes the position of the deflection mirror on the optical axis of the optic observation lens.

* * * * *